United States Patent [19]

Kato et al.

[11] Patent Number: 5,031,445

[45] Date of Patent: Jul. 16, 1991

[54] WATERPROOF TYPE OXYGEN SENSOR

[75] Inventors: Nobuhide Kato, Aichi; Masanori Katsu, Nagoya, both of Japan

[73] Assignee: NGK Insulators, Ltd., Aichi, Japan

[21] Appl. No.: 492,118

[22] Filed: Mar. 13, 1990

[30] Foreign Application Priority Data

Mar. 13, 1989 [JP] Japan .................................. 1-58023

[51] Int. Cl.$^5$ .......................................... G01N 27/409
[52] U.S. Cl. .................................. 73/23.310; 204/424
[58] Field of Search ........................... 73/23.31, 23.32; 204/424, 427, 428; 338/34; 422/94

[56] References Cited

U.S. PATENT DOCUMENTS

| 4,116,797 | 9/1978 | Akatsuka | 204/428 |
| 4,323,440 | 4/1982 | Akatsuka | 204/428 |
| 4,786,398 | 11/1988 | Wertheimer et al. | 204/424 X |
| 4,786,399 | 11/1988 | Wertheimer et al. | 204/424 X |
| 4,883,643 | 11/1989 | Nishio et al. | 204/424 X |
| 4,948,491 | 8/1990 | Kato et al. | 204/424 |

FOREIGN PATENT DOCUMENTS

| 0215607 | 3/1987 | European Pat. Off. | 204/427 |
| 133653 | 10/1981 | Japan | 204/424 |
| 168155 | 12/1981 | Japan | 204/424 |

*Primary Examiner*—Hezron E. Williams
*Assistant Examiner*—Joseph W. Roskos
*Attorney, Agent, or Firm*—Parkhurst, Wendel & Rossi

[57] ABSTRACT

An oxygen sensor for measuring an oxygen concentration in exhaust gases discharged from an automobile including an oxygen sensing element having inner and outer electrodes which communicate with the atmospheric air serving as a reference oxygen and the exhaust gases, and a tube-like metal cap in which the sensing element is arranged. Within a space formed between the sensing element and the metal cap are arranged first and second compressed talc members serving as gastight sealing sections to constitute a first space which is isolated from the exhaust gases by means of the first and second talc members and a second space which is isolated from the exhaust gases by means of the second talc member. In the metal cap is formed an opening which is communicated with the second space, so that a very small amount of the exhaust gases which might be introduced into the second space is discharged through the opening and is effectively prevented from being further introduced into the first space via the first talc member. The first space is communicated on one hand with a reference gas space into which the inner electrode of the sensing element is exposed and on the other hand with the surrounding atmospheric air by means of an air introducing section which is constructed to pass the air but does not allow passage of water therethrough.

18 Claims, 5 Drawing Sheets

FIG_1
PRIOR ART
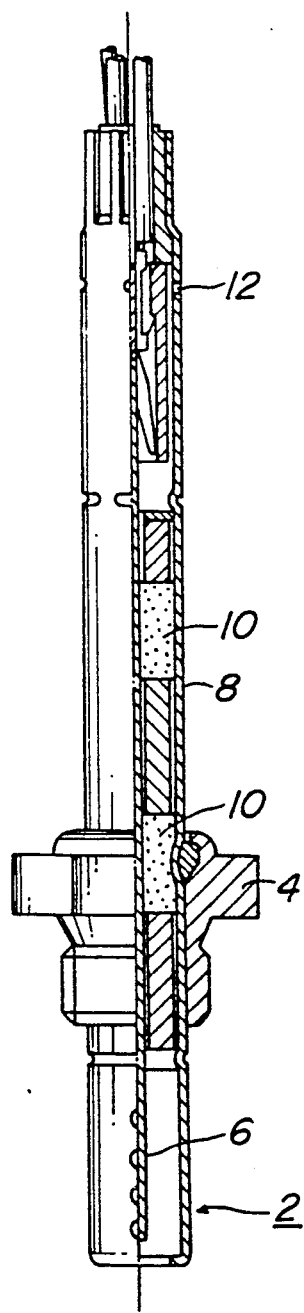

FIG_2
PRIOR ART
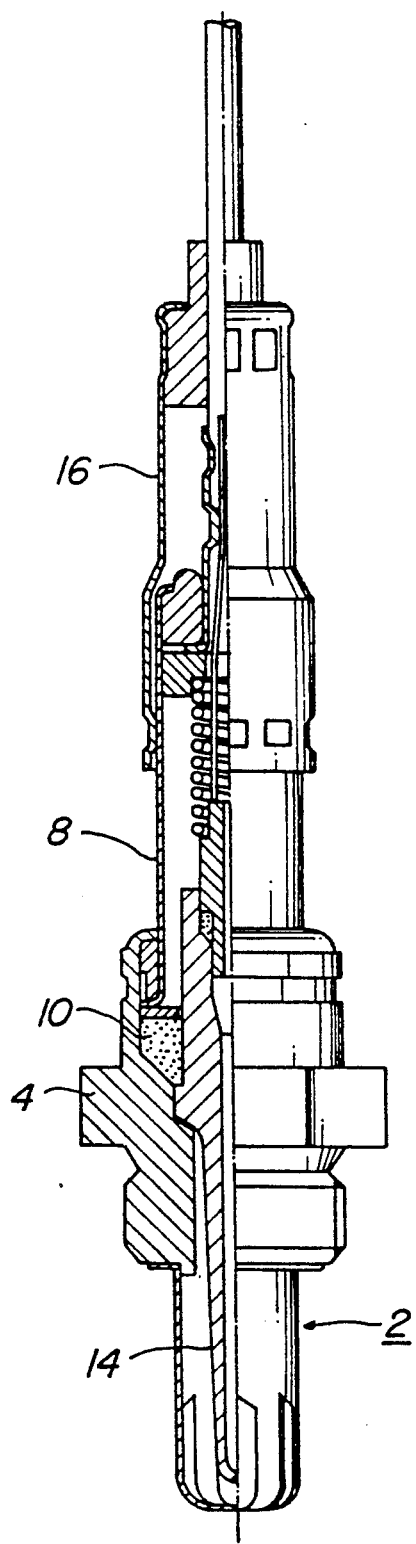

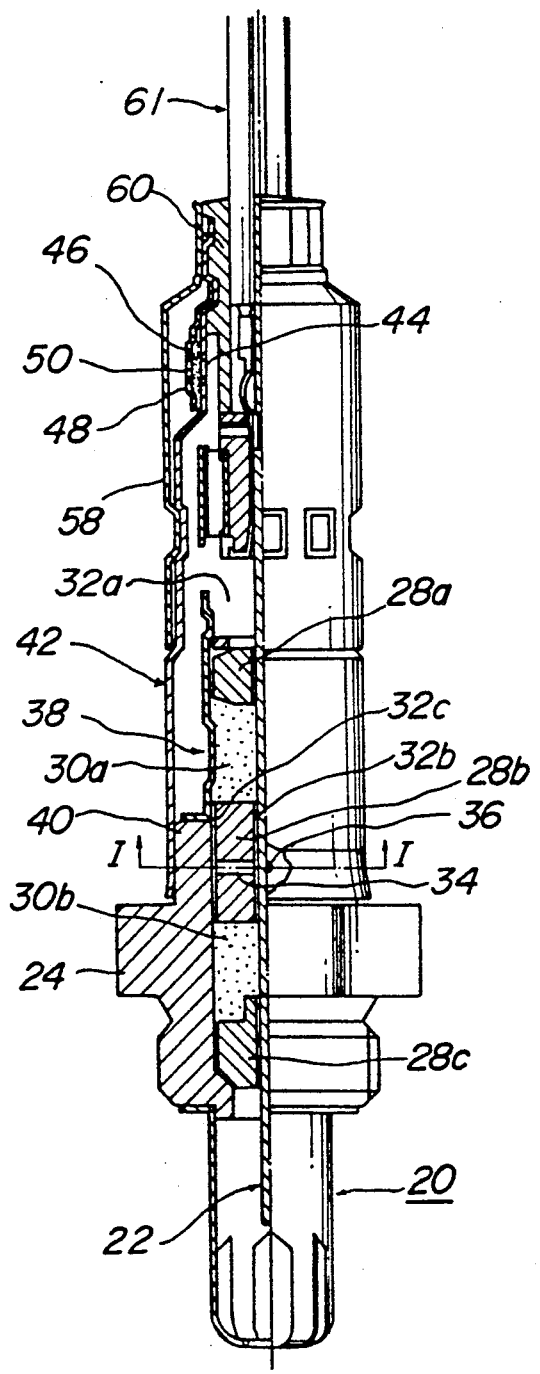
FIG._4a
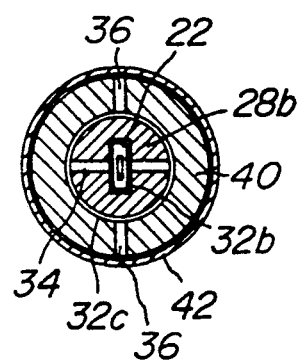
FIG._4b

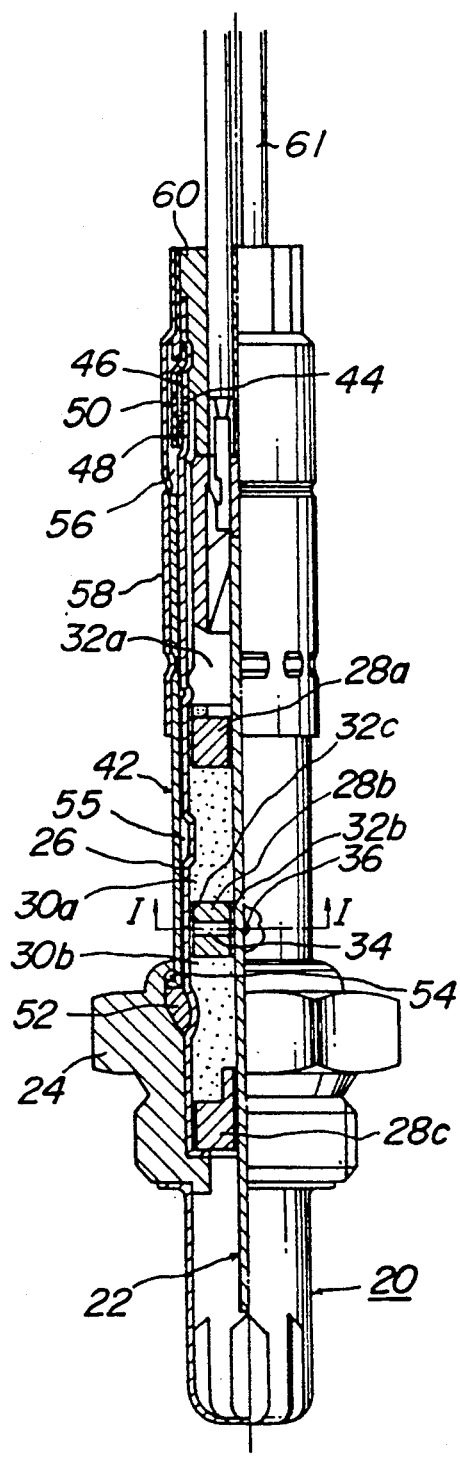
FIG_5a
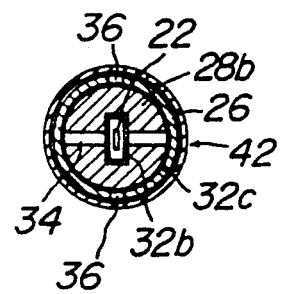
FIG_5b

WATERPROOF TYPE OXYGEN SENSOR

BACKGROUND OF THE INVENTION

Field of the Invention and Related Art Statement

The present invention relates to an oxygen sensor, and more particularly to a waterproof type oxygen sensor for measuring an oxygen concentration of exhaust gases discharged from an automobile. The oxygen sensor comprises an oxygen sensing element including inner and outer electrodes which are to be contacted with the atmospheric air and the exhaust gases, respectively, a tube-like metal cap for accommodating the oxygen sensing element, at least two gas-tightly sealing sections provided in the metal cap for isolating a reference gas space into which the inner electrode of the oxygen sensing element is exposed from the exhaust gases, and a communicating section for communicating the reference gas space with the surrounding atmospheric air.

The waterproof type oxygen sensor of the type mentioned in the preamble has been widely known as a detector for measuring an oxygen concentration in gases exhausted by an automobile. In the oxygen sensor of this type, the atmospheric air is generally used as a reference oxygen, and therefore the sensor is constructed to isolate the reference gas space into which the atmospheric air is introduced from the exhaust gases to be measured.

FIG. 1 is a half cross sectional view showing a known non-waterproof type oxygen sensor. The known oxygen sensor 2 shown in FIG. 1 comprises a metal housing 4 which accommodates a plate-shaped oxygen sensing element 6 and a metal cap 8. In order to separate the atmospheric air from the exhaust gases, in a space between the plate-like sensing element 6 and the metal cap 8 is filled with talc 10 which constitute gas-tight sealing sections. In this manner, an inner electrode of the oxygen sensing element 6 is isolated from the exhaust gases to be measured. At the same time, there is formed an air introduction passage for introducing the atmospheric air into the reference oxygen space within the oxygen sensor. In FIG. 1 this passage is constructed by an air communication opening 12 formed in the metal cap 8.

FIG. 2 illustrates another known non-waterproof type oxygen sensor 2 in which use is made of a test tube-shaped oxygen sensing element 14. In this known oxygen sensor, the above mentioned air introducing passage is formed by a space between the metal cap 8 and a metal boot 16 applied on the metal cap.

In the known oxygen sensors so far explained, when water intrudes into the reference gas space of the oxygen sensor, the water is vaporized to reduce a partial pressure of the reference oxygen, so that an electromotive force is decreased. In order to avoid such intrusion of water, various waterproof constructions have been prepared. For instance, an inner space between a stranded lead wire is used as the air introducing passage and a distal end of the passage which is provided at such a location that the water is not applied thereto is opened into the atmospheric air. Further, there is provided a water-repelling gap between the metal cap and the metal boot or a water-repelling porous member provided at an inlet opening of the air introducing passage.

However, it has been experimentally confirmed that when the known waterproof oxygen sensors are used for a long-term usage under high load-running conditions, the electromotive forces are decreased. As will be explained later in detail the inventors have found that the above mentioned decrease in the electromotive force is mainly caused by the intrusion of the exhaust gas into the reference gas space via the gas-tightly sealing section.

SUMMARY OF THE INVENTION

The present invention has for its object to provide a novel and useful waterproof type oxygen sensor which does not cause a serious drop in the electromotive force under high load-running conditions during a very long-term usage.

According to the invention, the waterproof type oxygen sensor for measuring a concentration of oxygen in exhaust gases comprises:

an oxygen sensing element having inner and outer electrodes which are to be contacted with atmospheric air and exhaust gases, respectively;

an accommodating means for accommodating said oxygen sensing element;

gas-tight sealing means including at least two gas-tight sealing sections provided within said accommodating means to form a first space which is isolated from the exhaust gases by said gas-tight sealing sections and is communicated with a reference gas space into which said inner electrode of the oxygen sensing element is exposed and at least one second space which is formed between said at least two gas-tight sealing sections and is isolated from the exhaust gases by at least one gas-tight sealing section on the side of the exhaust gases;

air introducing means formed in said accommodating means for communicating said first space with the surrounding atmospheric air and having a water-repelling function; and a communicating means provided in said accommodating means for communicating said at least one second space with the surrounding atmospheric air.

In the waterproof oxygen sensor according to the present invention, the exhaust gases which might invade the second space via at least one gas-tight sealing section can be predominantly discharged into the surrounding atmospheric air through the communicating means, so that the exhaust gases can be effectively prevented from invading the first space and being mixed with the atmospheric air which has been introduced into the first space as reference oxygen. In this manner, the decrease in the electromotive force can be avoided even under the high load-running conditions for a very long-term usage.

The inventors of the instant application have conducted various experiments and have confirmed that the drop in the electromotive force is caused by the following factors.

(a) When the air introducing passage is formed as the water-repelling passage, the gas permeability of the passage is decreased and the replacement of the reference gas, i.e. the atmospheric air with respect to the inner electrode is lowered.

(b) the gas-tightness of the gas-tight sealing section of the oxygen sensor is gradually decreased in the course of the long-term usage.

(c) When the oxygen sensor is continuously operated under high loads, the temperature of the oxygen sensor is increased and the gas-tightness of the gas-tight sealing members is deteriorated due to differences in thermal expansions between the sensing element and various parts such as the metal housing and metal cap.

(d) The concentration of reducing gas components, particularly a hydrogen gas component having a good diffusion property, in the exhaust gases is increased during the running at high load conditions, so that the reducing gas is liable to be introduced into the reference gas space of the oxygen sensor.

(e) When the pressure of the exhaust gases is increased, the exhaust gases are likely to invade the reference gas space within the oxygen sensor.

According to the present invention, at least one second space formed between at least two gas-tight sealing sections is communicated with the atmospheric air, so that the exhaust gases which might be introduced via at least one gas-tight sealing section on the side of the exhaust gases can be effectively discharged into the surrounding atmospheric air and therefore, the exhaust gases hardly invade the reference gas space via at least one gas-tight sealing section on the reference gas side. According to the invention, a flow rate of the exhaust gases passing from the second space through the air communicating means into the surrounding atmospheric air is made sufficiently larger than a flow rate of gases penetrating from the second space into the first space via at least one gas-tight sealing section on the reference gas side. Then the exhaust gases could hardly invade the reference gas space. It has been experimentally confirmed that the former flow rate is preferably made larger than the latter flow rate by at least ten times, particularly at least one hundred times.

The gas-tight sealing section on the reference gas side may be made of materials such as talc, cement and glass which provide a sufficiently small flow rate compared with the flow rate of the gases passing through the air communicating means provided between the second space and the atmospheric air.

It should be noted that according to the present invention, the waterproof air introducing means for introducing the surrounding atmospheric air into the reference gas space may be constructed by various means. For instance, this air introducing means may be formed by the above mentioned gaps formed between stranded wires of the lead conductor, a conduit formed within the lead conductor separately from the gaps between stranded wires, one or more water-repelling fine gaps and water-repelling porous members. It is preferable to form the air introducing means for communicating the reference gas space with the atmospheric air by the water-repelling fine gaps or the water-repelling porous members. This portion might be subjected to high temperature, so that it is sometimes difficult to use resins having an excellent water-repelling property In such a case, the air introducing means is not. provided in a main body of the oxygen sensor and the gap or gaps formed in the electrical lead conductor are preferably used as the air introducing means having the water-repelling function. In this case, the distal ends of the electrical lead conductors are provided at such a position where the water is not applied thereto. In such construction, the air introducing means becomes very long, so that the efficiency of replacing the reference gas with respect to the reference gas space is decreased more or less. However, even in such a case, according to the invention the exhaust gases do not invade the reference gas space, and therefore the decrease in the efficiency of the replacement of the reference gas, i.e. the atmospheric air does not cause a serious decrease in the output signal, i.e. the electromotive force.

BRIEF DESCRIPTION OF THE DRAWINGS

FIG. 1 is a half cross sectional and half front view showing the construction of a known non-waterproof oxygen sensor;

FIG. 2 is a half cross sectional and half front view illustrating another known non-waterproof oxygen sensor;

FIG. 4a is a partial cross sectional view illustrating another embodiment of the waterproof type oxygen sensor according to the invention, and FIG. 4b is a lateral cross sectional view cut along a line I—I in FIG. 4a; and FIG. 5a is a partial cross sectional view showing still another embodiment of the waterproof type oxygen sensor according to the invention and FIG. 5b is a lateral cross sectional view cut along a line I—I in FIG. 5a.

DESCRIPTION OF THE PREFERRED EMBODIMENTS

Figure 3A:
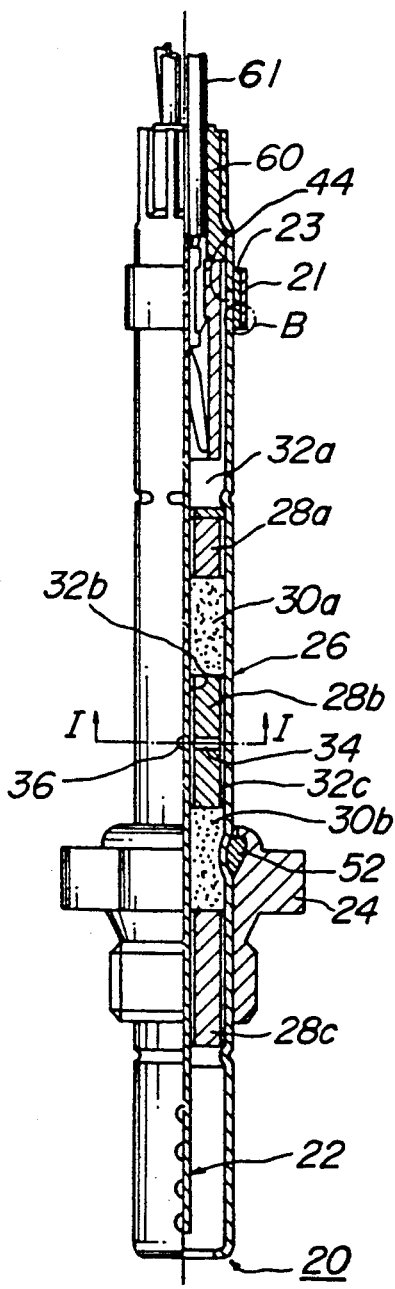
FIG. 3a is a partial cross sectional view showing an embodiment of the waterproof type oxygen sensor according to the invention.
Figure 3B:
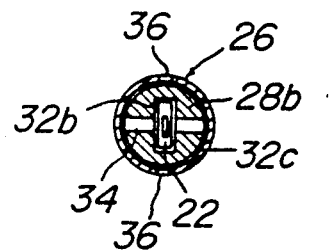
FIG. 3b is a lateral cross sectional view cut along a line I—I in FIG. 3a, and FIG. 3c is a schematical cross sectional view depicting the waterproof construction.
Figure 3C:
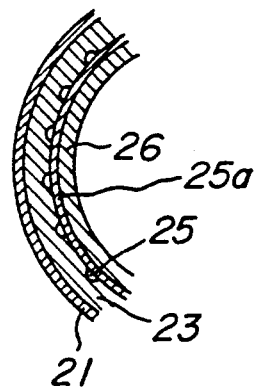

FIGS. 3a, 3b and 3c are half cross sectional and half front views showing an embodiment of the waterproof type oxygen sensor according to the invention. In FIG. 3a a right hand portion of the oxygen sensor is shown by a cross section, and FIG. 3b is a lateral cross sectional view cut along a line I—I in FIG. 3a. An oxygen sensor 20 of the present embodiment comprises a plate-shaped oxygen sensing element 22 which is secured to a tube-like metal cap 26 in a gas-tight manner by means of two talc members 30a and 30b provided between ceramic spacers 28a, 28b, 28c. In a lower end of the metal cap 26 there is formed an opening through which the exhaust gases are introduced into the oxygen sensor 20 and an upper end opening of the metal cap is closed by a rubber plug as will be explained later. The sensing element 22 is fixed in position by compressing talc powders. The first compressed talc 30a situated between the spacers 28a and 28b serves as a gas-tight sealing section on the side of the reference gases, and the second compressed talc 30b between the spacers 28b and 28c functions as a gas-tight sealing section on the side of the exhaust gases. By means of these gas-tight sealing sections 30a and 30b a space within the metal cap 26 is roughly divided into two spaces. That is to say, within the metal cap 26 there is formed a first space 32a situating above the talc 30a. It should be noted that the first space 32a is communicated with the reference gas space into which the inner electrode of the oxygen sensing element 22 is exposed. There is further formed a second space 32b between the gas-tight sealing sections 30a and 30b.

The first space 32a is isolated from the exhaust gases by means of the first and second gas-tight sealing sections 30a and 30b, and the second space 32b is separated from the exhaust gases by the second gas-tight sealing section 30b. Between the metal cap 26 and the spacer 28b, there is further formed a third space 32c. In the spacer 28b, there are formed lateral holes 34 which communicate the second and third spaces 32b and 32c with each other, so that the second and third spaces constitute the second space defined in claims of the present application. In the metal cap 26 there are formed two communication openings 36 at suitable positions with respect to the positions of outlets of the lateral holes 34. As best shown in FIG. 3b, an axis passing through the lateral holes 34 and an axis passing through the communication openings 36 are crossed with each other at right angles. It should be noted that the present invention is not limited to the above mentioned construction. In this manner, the second space 32b within the oxygen sensor is communicated with the external atmospheric air by means of the lateral holes 34, third space 32c and communication openings 36. The metal cap 26 is fixed to a housing 24 by means of a gas-tight ring 52, and in an upper end of the metal cap 26 is caulked a rubber plug 60 through which lead conductors 61 are extended. In this manner, the upper portion of the cap 26 is closed in an air-tight manner. The lead conductors 61 are connected to terminal electrodes of the oxygen sensing element 22.

FIG. 3c is an enlarged cross sectional view showing a portion B of the oxygen sensor 20 at which is provided the air introducing means for introducing the atmospheric air into the reference gas space communicated with the first space 32a. As illustrated in FIG. 3c, a water-repelling ring 23 is inserted between the cap 26 and a tube-like fixing member 21. An inner surface of the water-repelling ring 23 has a plurality of gaps 25. Onto a part of an outer surface of the metal cap 26 there is applied a water-repelling coating 25a in order to improve the water-repelling function. The fine gaps 25 are communicated with the first space 32a via openings 44 formed in the metal cap 26. According to the invention, the above mentioned gaps 25 are constructed such that they effectively repel the water, but allow the passage of the air.

In the oxygen sensor having the construction just explained above, a small amount of the exhaust gases passes through narrow gaps formed between the spacer 28c and the sensing element 22 and metal cap 26 and penetrates through the gas-tight sealing section 30b on the side of the exhaust gases into the second and third spaces 32b and 32c. The exhaust gases thus introduced into the second space 32b are discharged out of the communication openings 36 via the lateral holes 34 and the exhaust gases introduced into the third space 32c are directly discharged through the communication openings 36. Therefore, the exhaust gases hardly invade the first space 32a which serves as the reference gas space, so that the electromotive force is not decreased.

FIGS. 4a and 4b show another embodiment of the oxygen sensor according to the invention. In the present embodiment, portions similar to those shown in FIGS. 3a, 3b and 3c are denoted by the same reference numerals used in FIGS. 3a, 3b and 3c and their related explanation is dispensed with.

In the present embodiment, an oxygen sensing element 22 is fixed within metal housing 24 and inner metal tube-like member 38 secured to the housing by welding by means of gas-tight sealing sections formed by compressed talc member 30a and 30b filled in spaces between the spacers 28a, 28b and 28c. Similar to the previous embodiment, there are formed first, second and third spaces 32a, 32b and 32c above the talc 30a, between the spacer 28b and sensing element 22, and between the spacer 28b and housing 24, respectively. In the spacer 28b there are formed lateral holes 34 which communicate the second and third spaces 32b and 32c with each other. Further in an annular projection 40 of the housing 24 situating at a position corresponding to the spacer 28b, there are formed communication holes 36 for communicating the third space 32c with the surrounding atmospheric air. In order to protect the sensing element 22 from the environment a metal outer tube-like member 42 is clamped into the annular projection 40 of the housing 24 and is welded to the latter over its whole circumference. It should be noted that the welding seam has to be positioned above the communication holes 36. The lower end of the outer tube-like member 42 is widened outwardly from a position of the communication holes 36, so that the gas can be smoothly discharged out of the communication openings.

In an upper opening of the outer tube-like member 42 there is caulked a rubber plug 60 through which lead conductors 61 are extended to close the outer tube-like member in an air-tight manner. Further in the upper portion of the outer tube-like member 42 there are formed holes 44 for communicating the inside of the member 42 with the atmospheric air. Around the outer periphery of the holes 44 is arranged a water-repelling porous member 46 which is further covered with a metal fixing tube 48. That is to say, upper and lower edges of the fixing tube 48 are caulked to fix the water-repelling porous member 46. In the fixing tube 48 there are also formed holes 50 for communicating the inside of the tube with the atmospheric air. There is further provided a metal boot 58 which covers the fixing tube 48. Therefore, the atmospheric air is introduced into a gap between the metal boot 58 and outer tube-like member 42, passes through the holes 50, porous member 46 and holes 44 successively, and then is introduced into the first space 32a which is communicated with the reference gas space into which the inner electrode of the oxygen sensing element 22 is exposed.

In the present embodiment, the outer tube-like member 42 is provided on the communication holes 36 formed in the annular projection 40 of the housing 24 in such a manner that the communication of gas is not affected, so that the waterproof function is superior to that of the first embodiment. Therefore, even if the oxygen sensor is subjected to the water, the water is hardly introduced into the reference air space within the oxygen sensor via the communication holes 36 formed in the annular projection 40 of the housing 24 so that the decrease in the electromotive force can be further effectively prevented. This is due to the fact that the water which might be introduced into the second space 32b, third space 32c and lateral holes 34 via the communication holes 36 is effectively prevented from being introduced into the first space of the reference gas with the aid of the gas-tight sealing section 30a on the reference gas side. From the above point of view it is preferable to construct the gas-tight sealing section 30a on the reference gas side by materials having a low water absorbance such as glass or compressed talc. In the present embodiment, the talc 30a on the reference gas side is further compressed by partially constricting the inner tube-like member 38, so that the gas-tightness of the talc 30a is further increased. Therefore, a very small amount of the exhaust gases which might be introduced into the second and third spaces 32b and 32c via the talc 30b on the side of the exhaust gases can be effectively prevented from being introduced into the first space communicated with the reference gas space.

FIGS. 5a and 5b are cross sectional views showing still another embodiment of the oxygen sensor according to the invention. Also in this embodiment, portions similar to those of the previous embodiments are denoted by the same reference numerals used in the previous embodiments, and their construction is not explained in detail. The present embodiment differs from the second embodiment in a point that the talcs 30a and 30b and the spacers 28a, 28b and 28c are fixed in position within the metal cap 26 in the air-tight manner, and the metal cap 26 is fixed to the housing 24 by means of a gas-tight ring 52. Further the metal outer tube-like member 42 is fixed to the housing 24 by means of a fixing ring 54. By constructing the oxygen sensor in the manner just explained above, the gas-tightness is further improved and the intrusion of the exhaust gases into the reference gas space can be prevented in an effective manner.

The communication openings 36 for escaping the exhaust gases are formed in the metal cap 26, and a space 55 is formed between the outer tube-like member 42 and the cap 26, said space being communicated with a space 56. This space 56 is communicated with the surrounding atmospheric air via a gap formed between the tube-like member 42 and a metal boot 58. Therefore, the exhaust gases discharged from the communication openings 36 are discharged into the atmospheric air by means of the spaces 55 and 56 and the gap between the member 42 and the boot 58. In the cap 26 there is formed the communicating section for communicating the first space 32a with the surrounding atmospheric air. This communicating section consists of the air communicating holes 44 and 50, water-repelling porous member 46 and fixing member 48. In this manner, the gas-tightness of the gas-tight sealing sections can be improved, while the waterproof nature of the oxygen sensor is not deteriorated.

The present invention is not limited to the embodiments explained above, but many modifications and alternations may be conceived by those skilled in the art within the scope of the invention. In the embodiments so far explained, use is made of the plate-shaped oxygen sensing element, but the present invention may be equally applied to the test tube-like oxygen sensing element. Further the gas-tight sealing sections may be formed by other materials than the talc such as cement, glass and metal packing. The air communicating member is formed by the water-repelling porous material, but it may be formed by compressed glass fibers, compressed glass fibers on which a water-repelling material is coated, compressed graphite fibers, compressed graphite fibers on which a water-repelling material is coated, a porous metal on which a water-repelling material is coated, compressed metal fibers on which a water-repelling material is coated, and any other material having air permeable and water-repelling function. Further, the present invention may be also applied to oxygen sensors having waterproof air communication passages which are formed by water-repelling materials having fine spaces, gaps between stranded lead wires, and lead wires in which a separate air introducing passage is formed.

As explained in detail, in the waterproof oxygen sensor according to the invention, at least one second space formed between the at least two gas-tight sealing sections is communicated with the surrounding atmospheric air, so that the exhaust gases which invade the second space via the gas-tight sealing section on the side of the exhaust gases can be discharged effectively out of the second space and the exhaust gases effectively are prevented from being introduced into the first space which is communicated with the reference gas space via the gas-tight sealing section on the reference gas side. Therefore, a desired electromotive force can be obtained by a small replacement of the reference air and the desired electromotive force can be maintained stably under high load-running conditions for a very long-term usage.

What is claimed is:

1. A waterproof oxygen sensor for measuring an oxygen concentration in exhaust gases comprising:
   an oxygen sensing element having inner and outer electrodes which are to be contacted with atmospheric air and exhaust gases, respectively;
   accommodating means for accommodating said oxygen sensing element;
   gas-tight sealing means including at least two gas-tight sealing sections provided within said accommodating means to form a first space which is isolated from the exhaust gases by said at least two gas-tight sealing sections and is communicated with a reference gas space into which said inner electrode of said oxygen sensing element is exposed, and at least one second space formed within said accommodating means between said at least two gas-tight sealing sections, said second space being isolated from the exhaust gases by at least one gas-tight sealing section on a side of the exhaust gases;
   air introducing means formed in said accommodating means for communicating said first space with surrounding atmospheric air, said air introducing means being water repellent; and
   air communicating means provided in said accommodating means for communicating said at least one second space with surrounding atmospheric air.

2. An oxygen sensor according to claim 1, wherein said accommodating means comprises a tube-like metal cap in which said oxygen sensing element is arranged, a housing for supporting the metal cap, and at least three spacers which are arranged on both sides of each of said at least two gas-tight sealing sections, respectively, and said air communicating means comprises at least one hole formed in at least one spacer arranged between said at least two gas-tight sealing sections such that exhaust gases introduced into said second space via said at least one gas-tight sealing section are discharged into the surrounding atmospheric air by means of said hole.

3. An oxygen sensor according to claim 2, wherein said air communicating means further comprises at least one opening formed in said metal cap.

4. An oxygen sensor according to claim 3, wherein said hole formed in said at least one spacer and said opening formed in said metal cap are formed such that axes passing through said hole and said opening intersect at substantially right angles.

5. An oxygen sensor according to claim 2, wherein said air communicating means further comprises at least one hole formed in said housing.

6. An oxygen sensor according to claim 2, wherein said air introducing means comprises at least one opening formed in said metal cap at such a position that said at least one opening is communicated with said first space, and a ring-shaped member arranged on the metal cap to cover said at least one opening, said ring-shaped member having formed therein a plurality of fine gaps which are communicated with said at least one opening.

7. An oxygen sensor according to claim 2, wherein said air introducing means comprises at least one opening formed in said metal cap at such a position that said at least one opening is communicated with said first space, and a water repellent, air-permeable ring-shaped member arranged on the metal cap to cover said at least one opening.

8. An oxygen sensor according to claim 7, wherein said ring-shaped member is formed by a compressed member of glass fibers.

9. An oxygen sensor according to claim 7, wherein said ring-shaped member is formed by a compressed member of glass fibers on which a water-repellent material is coated.

10. An oxygen sensor according to claim 7, wherein said ring-shaped member is formed by a compressed member of graphite fibers.

11. An oxygen sensor according to claim 7, wherein said ring-shaped member is formed by a compressed member of graphite fibers on which a water-repellent material is coated.

12. An oxygen sensor according to claim 7, wherein said ring-shaped member is formed by a porous metal member on which a water-repellent material is coated.

13. An oxygen sensor according to claim 7, wherein said ring-shaped member is formed by a compressed member of metal fibers on which a water-repellent material is coated.

14. An oxygen sensor according to claim 1, wherein said gas-tight sealing means comprises a first gas-tight sealing section arranged within said accommodating means on a side of said reference gas space and a second gas-tight sealing section arranged within said accommodating means on a side of an exhaust gas space, said first and second gas-tight sealing sections having a first flow rate of exhaust gases passing from said second space though said air communicating means into the surrounding atmospheric air which is at least ten times larger than a second flow rate of gases penetrating from said second space through said first gas-tight sealing section into said first space.

15. An oxygen sensor according to claim 14, wherein said first flow rate of said first and second gas-tight sealing sections is at least one hundred times larger than said second flow rate.

16. An oxygen sensor according to claim 14, wherein said first and said second gas-tight sealing sections are formed of compressed talc powders.

17. An oxygen sensor according to claim 14, wherein said first gas-tight sealing section is formed of glass.

18. An oxygen sensor according to claim 14, wherein said first gas-tight sealing section is formed of metal.

* * * * *